US007236832B2

(12) United States Patent
Hemmerling et al.

(10) Patent No.: US 7,236,832 B2
(45) Date of Patent: Jun. 26, 2007

(54) NEUROMUSCULAR MONITORING USING PHONOMYOGRAPHY

(75) Inventors: Thomas Hemmerling, Montreal (CA); Pierre A. Mathieu, Montreal (CA); Francois Donati, Montreal (CA); Guillaume Trager, Montreal (CA); Robert Guardo, Mont St-Hilaire (CA); Denis Babin, Longueuil (CA); Chang Bou-Phon, Ville Saint-Laurent (CA)

(73) Assignees: Val-Chum, Societe en Commandite, Montreal, Quebec (CA); Universite Montreal, Montreal, Quebec (CA); Corporation l'Ecole Polytechnique de Montreal, Montreal, Quebec (CA)

( * ) Notice: Subject to any disclaimer, the term of this patent is extended or adjusted under 35 U.S.C. 154(b) by 68 days.

(21) Appl. No.: 10/730,811

(22) Filed: Dec. 8, 2003

(65) Prior Publication Data

US 2004/0254617 A1    Dec. 16, 2004

Related U.S. Application Data

(60) Provisional application No. 60/431,736, filed on Dec. 9, 2002.

(51) Int. Cl.
 *A61N 1/00* (2006.01)
(52) U.S. Cl. ...................................... 607/48
(58) Field of Classification Search ............ 607/48, 607/49; 600/485–499
 See application file for complete search history.

(56) References Cited

U.S. PATENT DOCUMENTS

2002/0099296 A1*  7/2002  Flaherty et al. ............. 600/485
2002/0173828 A1* 11/2002  Gozani et al. ................ 607/48

OTHER PUBLICATIONS

Sneyd, "Extended Neuromuscular Blockade with Mivacurium Following Pancuronium", European Journal of Anaesthesiology, vol. 13, 1996, pp. 483-484.

Hemmerling TM, Babin D, Donati F. Photomyography and Mechanomygraphy can be used interchangeably to measure neuromuscular block at the corrugator supercilii muscle (Phonomyography as a novel method to determin neuromuscular blockade at the laryngeal adductor muscles): comparison with the cuff-pressure method. The Journal of the American Society of Anesthesiologists, Inc., Anesthesiology V 98, No. 2, Feb. 2003, pp. 359-363.

Hemmerling TM, Babin D, Donati F. "Phonomyography and Mechanomygraphy can be used interchangeably to measure neuromuscular block at the adductor pollicis muscle", The Journal of the American Society of Anethesiologists, Inc. Anesth Anaig 2004; 98: pp. 377-381.

Donati, "Neuromuscular blocking drugs for the new millennium: current practice, future trends—comparative pharmacology of neuromuscular blocking drugs," Anesth. Analg., May 2000; 90(5 Suppl); pp. S2-S6.

Ibebunjo et al., "Morphological correlates of the differential responses of muscles to vecuronium," Br. J. Anaesth., Aug. 1999; 83(2); pp. 284-291.

(Continued)

Primary Examiner—George Manuel
(74) Attorney, Agent, or Firm—Fay Kaplun & Marcin, LLP (57) ABSTRACT

A neuromuscular monitoring system comprises at least one neurostimulator to apply muscle-activating stimulation signals to a patient's body via at least one electrode, and at least one pressure waveform sensor to detect pressure waveform signals produced by a patient's muscle in response to the applied stimulation signals. The detected pressure waveform signals are processed and data related to these detected pressure waveform signals are displayed. A method for neuromuscular monitoring using pressure waveform sensors is also described.

23 Claims, 7 Drawing Sheets

OTHER PUBLICATIONS

Engback, "Monitoring of neuromuscular transmission by electromyography during anaesthesia. A comparison with mechanomyography in cat and man," Dan. Med. Bull, Sep. 1996; 43(4); pp. 301-16. [abstract].

Hemmerling et al., "Phonomyography of the corrugator supercilii muscle: signal characteristics, best recording site and comparison with acceleromyography," Br. J. Annesth., Mar. 2002; 88(3); pp. 389-393.

Plaud et al., "The corrugator supercilii, not the orbicularis oculi, reflects rocuronium neuromuscular blockade at the laryngeal adductor muscles," Anesthesiology, Jul. 2001; 95(1); pp. 96-101.

Rimaniol et al., "A comparison of the neuromuscular blocking effects of atracurium, mivacurium, and vecuronium on the adductor pollicis and the orbicularis oculi muscle in humans," Anesth. Analg., Oct. 1996; 83(4); pp. 808-813.

McClusky et al., "A comparison of acceleromyography and mechanomyography for determination of the dose-response curve of rocuronium in children," Anaesthesia, Apr. 1997; 52(4); pp. 345-349.

Mortensen et al., "Perioperative monitoring of neuromuscular transmission using acceleormyography prevents residual neuromuscular block following pancuronium," Acta. Anaesthesiol. Scand., Aug. 1995; 39(6); pp. 797-801.

Frangioni et al., "The mechanism of low-frequency sound production in muscle," Biophys. J., May 1987; 51(5); pp. 775-783.

Dascalu et al., "Acoustic monitoring of intraoperative neuromuscular block," Br. J. Anaesth., Sep. 1999; 83(3); pp. 405-409.

Bellemare et al., "Temporal relation between acoustic and force responses at the adductor pollicis during nondepolarizing neuromuscular block," Anesthesiology, Sep. 2000; 93(3); pp. 646-652.

Hemmerling et al., "Phonomyography of the corrugator supercilii muscle: signal characteristics, best recording sire and comparison with acceleromyography," Br. J. Anaesth., Mar. 2002; 88 (3); pp. 389-393.

Hemmerling et al., "Duration of control stimulation does not affect onset and offset of neuromuscular blockade at the corrugator sueprcilii muscle measured with phonomyography or acceleromyography." Can. J. Anaesth., 2002; 49(9); pp. 913-917.

Hemmerling et al., "Intraoperative monitoring of the recurrent laryngeal nerve in 151 consecutive patients undergoing thyroid surgery," Anesth. Analg., Aug. 2001; 93(2); pp. 396-399.

Kastl et al., "Electromyographic nerve identification during resection of an intrathoracic goiter via a right anterolateral thoracotomy using a novel method," Surgery, Jul. 2001; 130(1): pp. 93-96.

Hemmerling et al., [Intraoperative electromyographicidentification of recurrence as a routine procedure] Chirurg, May 2000; 71(5); pp. 545-550. [German document with English abstract].

Datex Ohmeda S-5, Neuromuscular Transmission Module, M-NMT, 2 sheets.

Bluestar Enterprises: TOF Watch, www.bluestarent.com/tofwatch/twside.htm, 2 sheets.

Sherrer et al., "Accelerometry as a Neuophysiologic Method of Exploring Neuromusuclar Activity", Laval Med, vol. 40 No. 4, Apr. 1969, pp. 348-352 * .

* cited by examiner

FIG. 1

FIG_2A

FIG. 2B

FIG_3

FIG. 4A

FIG_4B

NEUROMUSCULAR MONITORING USING PHONOMYOGRAPHY

PRIORITY CLAIM

The Application claims benefit of the U.S. Provisional Application Ser. No. 60/431,736 filed on Dec. 9, 2002 which is expressly incorporated herein, by reference.

FIELD OF THE INVENTION

The present invention relates to the use of phonomyography for performing neuromuscular monitoring.

The present specification will refer to many references listed at the end of the disclosure, these references being herein incorporated by reference.

BACKGROUND OF THE INVENTION

Neuromuscular monitoring, the monitoring of muscle relaxation, is as essential as controlling blood pressure or heart rate during surgery. A patient who is extubated when still partially relaxed is at great risk of respiratory complications. Also, a patient incompletely relaxed during surgery can endanger the success of surgery.

Since muscle relaxants are an important cost factor in anesthetic drug selection, neuromuscular monitoring also helps to titrate the exact dosing of muscle relaxants required during surgery. Further applications of neuromuscular monitoring are in intensive care units where peripheral neuropathies with impaired muscle function play an essential role in morbidity of long-term ventilation; repetitive and objective neuromuscular monitoring could help to control and monitor this problem.

Unfortunately, despite these facts, knowledge about the action of muscle relaxants is still quite limited and the tools to measure their function in daily routine are even more limited.

Ideally, (a) neuromuscular function should be easily monitored for all physiologically important muscles in a non-invasive and reliable way, (b) a neuromuscular method and easy-to-use monitoring device should be available to give precise and reliable information about the state of neuromuscular transmission at any given time during surgery, and finally (c) reliable data should be established for any given muscle relaxant on onset, offset and peak effect for different muscles.

During the last 15 years, neuromuscular research and especially neuromuscular monitoring has been the object of important developments. The most important discovery in neuromuscular research has been the understanding that onset, peak effect and offset of neuromuscular blockade after injection of a muscle relaxant are different for different muscles [1]. This is not only due to different circulation times, but also to specific morphological differences of different muscles [2], such as acetylcholine receptor densities and distribution and the type of muscle fibers predominant in a given muscle. This discovery meant that the monitoring of only one, easily accessible muscle, such as the adductor pollicis muscle, was no longer valid to reflect muscle relaxant action in the human body. p The last 15 years were spent to develop methods for monitoring different muscles, such as the larynx, the diaphragm or the eye muscles. This lead to the discovery that the effect of a bolus dose of muscle relaxant at the larynx and diaphragm produces a less pronounced effect in comparison to the adductor pollicis muscle, and a shorter onset and offset of neuromuscular blockade [1]. Although these discoveries were important for research, clinical monitoring of more central, but nevertheless important muscles during surgery (e.g. abdominal surgery) and/or anesthetic relaxation (e.g. intubation) was impaired by the fact that most methods were unsuited for clinical use.

All methods for monitoring muscle relaxation are based on the principle of electric stimulation of a motor nerve and monitoring the reaction of the evoked muscle contraction either directly by measuring the actual force created (mechanomyography) or indirectly by measuring electric potentials at the muscle occurring before the actual muscle contraction (electromyography) or the acceleration of the muscle contraction (acceleromyography).

A fundamental problem of all these research efforts of comparing neuromuscular blockade at different muscles remained that the gold standard of neuromuscular monitoring, mechanomyography which measures the actual force of muscle contraction, cannot be applied to all muscles.

Neuromuscular monitoring using electromyography (measuring the electric potential created by muscle contraction) is generally unreliable and results obtained using this method cannot be used interchangeably with mechanomyography [3]. It is believed that there is currently no electromyographic monitor used in clinical routine.

Acceleromyography measures the acceleration of movement created by muscle contraction. Acceleromyography has been used in research and clinical routine for more than a decade and there are still fundamental problems which have inhibited widespread use of this technique. For example:

This technique can only be used to measure neuromuscular blockade at the adductor pollicis muscle and not reliably at any other muscle (e.g. eye muscles) [4];

The results obtained using this technique are dependent on the exact position of the hand; and the use of this technique is cumbersome and commercially available monitors give very little information, especially no display of the original evoked signals.

Especially the eye muscles are prone to these problems: the corrugator supercilii muscle is an interesting small muscle that is responsible for vertical frowning. The corrguator supercilii muscle correlates well with the adducting laryngeal muscles in terms of onset and offset of neuromuscular blockade [5]. For clinical routine, acceleromyography has been well established as a method to monitor neuromuscular blockade at the adductor pollicis muscle [6]; however, there are some studies questioning its validity in comparison to mechanomyography [7] and it is mostly used to monitor recovery from neuromuscular blockade [8].

Because of the above technical problems, most clinicians still rely on the simple tactile or visual estimation of neuromuscular blockade. Although this might be clinically acceptable when recovery from operation block is judged, it is clearly not objective and cannot be used to titrate neuromuscular blockade during surgery.

The present invention provides a method and device using phonomyography for conducting neuromuscular monitoring, in order to overcome at least in part the drawbacks and limitations of the above discussed prior devices and methods.

SUMMARY OF THE PRESENT INVENTION

An object of the present invention is to provide neuromuscular monitoring using phonomyography, to overcome at least in part the drawbacks and limitations of the above discussed devices and methods.

More specifically, in accordance with one aspect of the present invention, there is provided a neuromuscular monitoring system using phonomyography, comprising means for applying muscle-activating stimulation signals to a patient's body via at least one electrode, means for sensing pressure waveform signals produced by a patient's muscle in response to the applied stimulation signals, and means for processing the sensed pressure waveform signals and means for displaying data, from the processing means, related to the sensed pressure waveform signals.

According to another aspect of the present invention, there is provided a neuromuscular monitoring system using phonomyography, comprising at least one neurostimulator to apply muscle-activating stimulation signals to a patient's body via at least one electrode, at least one pressure waveform sensor to detect pressure waveform signals produced by a patient's muscle in response to the applied stimulation signals, and a processor of the detected pressure waveform signals and a display of data, from the processor, related to the detected pressure waveform signals.

According to a further aspect of the present invention, there is provided a neuromuscular monitoring method using phonomyography, comprising providing at least one pressure waveform sensor, positioning the at least one pressure waveform sensor at a predetermined position of a patient's body, providing at least one electrode, positioning the at least one electrode at a predetermined position of the patient's body, applying muscle-activating stimulation signals to the patient's body via the at least one electrode, sampling pressure waveform signals detected by the at least one pressure waveform sensor in response to the applied muscle-activating stimulation signals, processing the detected pressure waveform signals, and displaying data, from the act of processing, related to the detected pressure waveform signals.

Finally, a still further aspect of the present invention is concerned with a neuromuscular monitoring method using phonomyography, comprising:
providing at least one pressure waveform sensor;
positioning the at least one pressure waveform sensor at a predetermined position of a patient's body;
providing at least one electrode;
positioning the at least one electrode at a predetermined position of the patient's body;
applying a muscle-activating stimulation signal to the patient's body via the at least one electrode;
sampling a pressure waveform signal detected by the at least one pressure waveform sensor in response to the applied muscle-activating stimulation signal;
measuring a reference amplitude ($A_{ref}$) of the sampled signal;

after a relaxant has been administered:
applying a subsequent muscle-activating stimulation signal to the patient's body via the at least one electrode;
sampling a subsequent pressure waveform signal detected by the at least one pressure waveform sensor in response to the subsequent muscle-activating stimulation signal;
measuring an amplitude (A) of the subsequent pressure waveform signal;
calculating a ratio $A/A_{ref}$; and
displaying the calculated ratio.

The foregoing and other objects, advantages and features of the present invention will become more apparent upon reading of the following non restrictive description of illustrative embodiments thereof, given by way of example only with reference to the accompanying drawings.

DETAILED DESCRIPTION OF THE ILLUSTRATIVE EMBODIMENTS

Muscle contraction creates pressure waveforms. Phonomyography is the detection of these pressure waveforms with a low frequency sensitive microphone acting as a pressure waveform sensor [9]. Detection of these pressure waveforms through phonomyography can be used to determine neuromuscular blockade [[4], [10] and [11]]. Since the amplitude of the sound waves detected at the microphone is a function not only of stiffness and tension of the muscle, but also of the distance and type of the tissue separating the muscle and the recording microphone, the position of the microphone in relation to the muscle and the monitored muscle affects the signal characteristics [9].

In the illustrative embodiments of the present invention, phonomyography is used as a method for monitoring neuromuscular blockade at all muscles of interest. It is believed that phonomyography could become a new standard of neuromuscular monitoring for research and clinical routine. Phonomyography has shown to be superior to acceleromyography for monitoring neuromuscular blockade at the corrugator supercilii muscle [4], the small muscle around the eye that is easily accessible for monitoring and that reflects muscle relaxation of more central muscles such as larynx, abdominal muscles and diaphragm. Phonomyography has further shown minimal bias and very good agreement with mechanomyography at the adductor pollicis muscle, larynx and the corrugator supercilii muscle.

Figure 1:
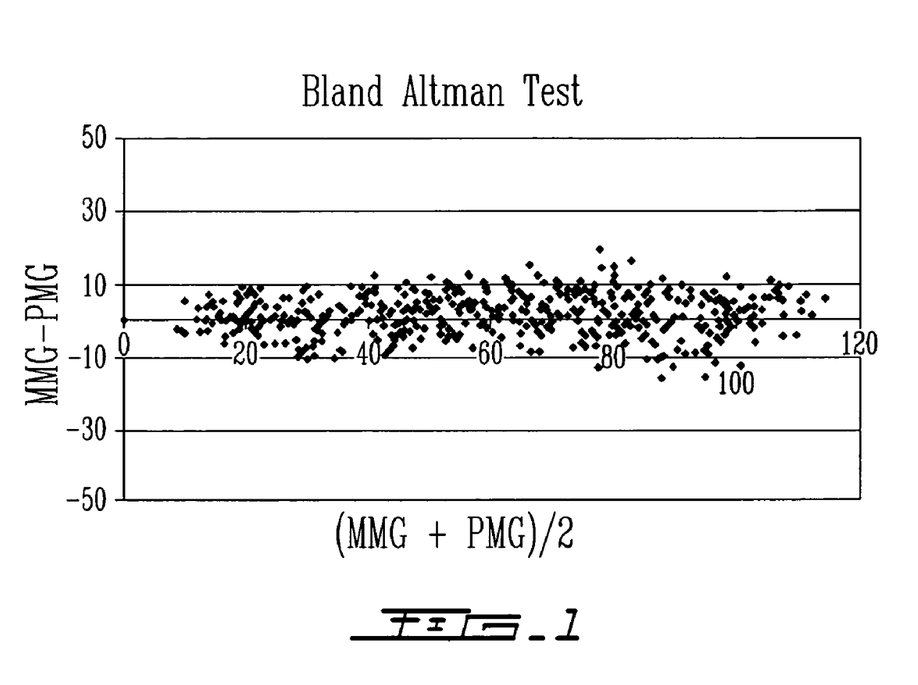
FIG. 1 is a graph of a Bland Altman Test for the adductor pollicis muscle.

Phonomyography has been compared to mechanomyography for the larynx, adductor pollicis muscle and corrugator supercilii muscle. Mean bias was low between the two methods and limits of agreement narrow (larynx [14]; corrugator supercilii muscle [15]; and adductor pollicis muscle [16]. FIG. 1 is a graph of a Bland Altman Test for the adductor pollicis muscle. FIG. 1 shows that mean bias between phonomyography and mechanomyography was 0% with limits of agreement of −10% and +10% of twitch height (T1) (mechanomyography minus phonomyography) [16].

Figure 2A:
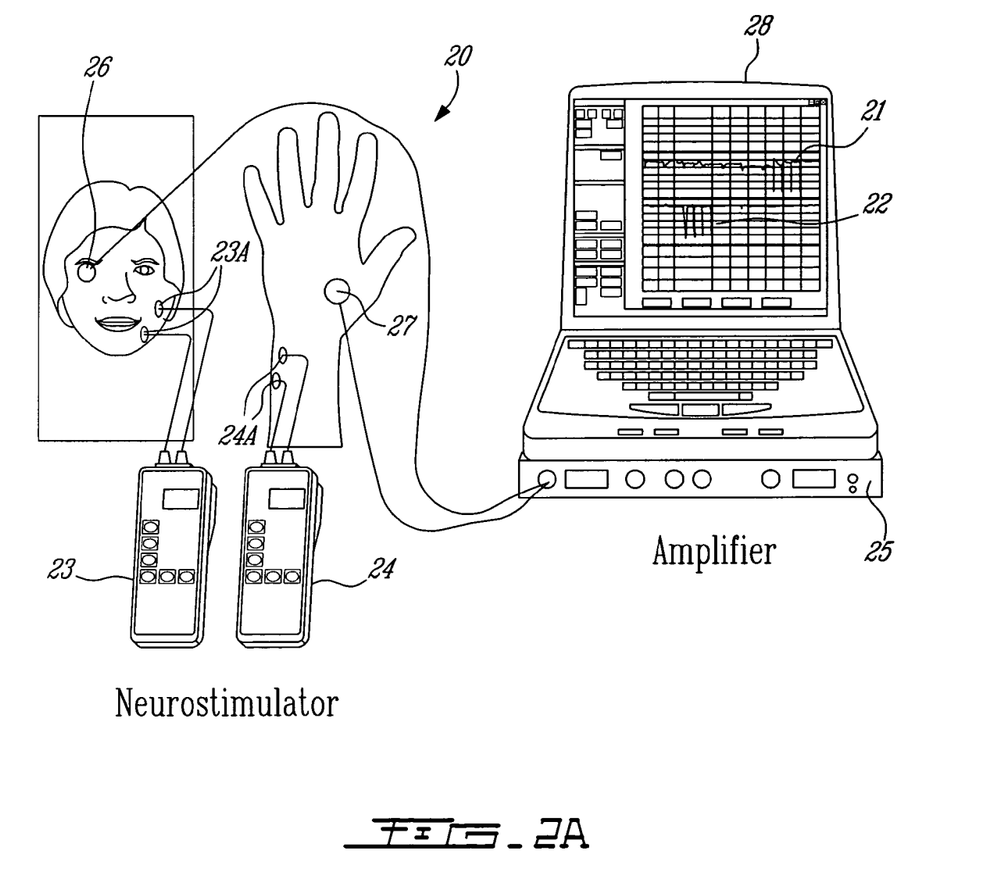
FIG. 2A is a schematic diagram of a first illustrative embodiment of a phonomyographic device for neuromuscular monitoring according to the present invention.

FIG. 2A is a schematic diagram of a first illustrative embodiment of a phonomyographic device 20 according to the present invention. As illustrated in FIG. 2A, the phonomyographic device 20 is able to detect, process and display the original phonomyographic signals 21 and 22 of two different muscles (see the screen of the laptop computer 28 in FIG. 2A).

As shown in FIG. 2A, the phonomyographic device 20 comprises:

two different, left and right neurostimulators 23 and 24 for simultaneously stimulating the facial (left) and ulnar (right) nerves via respective electrodes 23A and 24A, for example by means of typical train-of-four twitches (not shown);

a phonomyographic amplifier 25 for amplifying phonomyographic signals respectively detected through pressure waveform sensors 26 and 27 from the corrugator supercilii muscle (left) and the adductor pollicis muscle (right); and a controller, in the form of a laptop computer 28 for processing and displaying the two phonomyographic signals 21 and 22.

As will easily be understood by one of ordinary skill in the art, the amplifier 25 and the laptop computer 28 could be embodied together in a custom made controller (not shown).

The current knowledge suggests that the corrugator supercilii muscle might be a better indicator of neuromuscular blockade at central muscles [4], such as the larynx or the diaphragm. The adductor pollicis muscle is the standard muscle to judge sufficient recovery of neuromuscular blockade at slowly recovering muscles and is an indicator of neuromuscular blockade at extremity muscles. It is believed that the display of raw signals is of additional benefit since it is less prone to artifacts than digitized data—as used in the commercial acceleromyographic devices—and gives a more complete picture of the neuromuscular blockade.

Figure 2B:
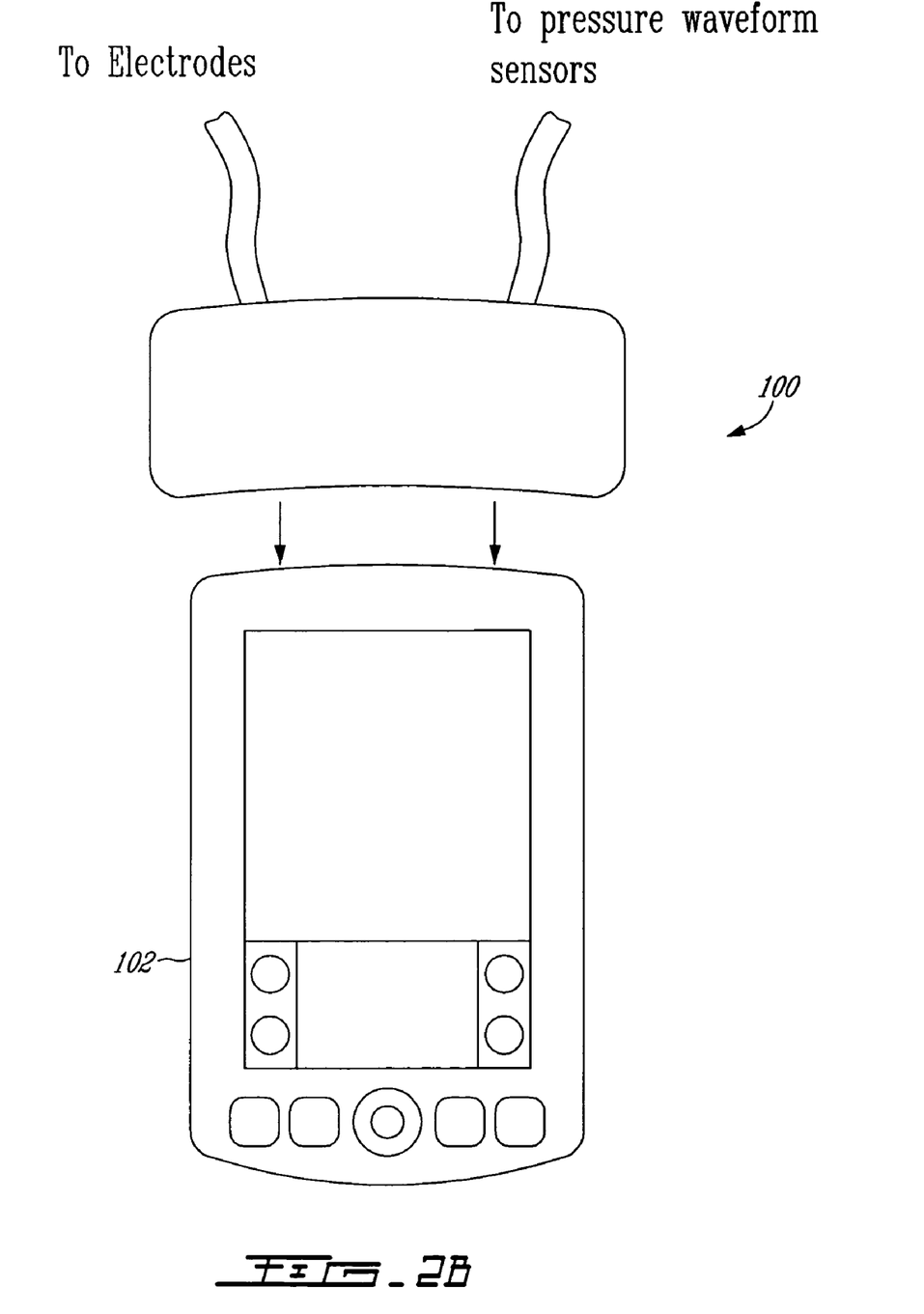
FIG. 2B is a schematic diagram of a handheld illustrative embodiment of a phonomyographic device for neuromuscular monitoring according to the present invention.

Turning now to FIG. 2B of the appended drawings, a second illustrative embodiment 100 of phonomyographic device according to the present invention is miniaturized and integrates the neurostimulators as well as parallel traces of digitalized data, such as a T4/T1 ratio displayed in real time. The T4/T1 ratio is the ratio between the peak-to-peak amplitude of the phonomyographic response of the muscle to the fourth stimulation pulse of a train-of-four versus the peak-to-peak amplitude of the phonomyographic response of the muscle to the first stimulation pulse of the train-of-four.

The phonomyographic device 100 is a module that may be connected to a pocket PC, such as a Palm Pilot™ 102, to use its computing power and its display. The basic idea is that the actual screen module is not bigger than a pocket PC. A change of microphones (different sizes for different muscles could be used) and/or stimulator probes is also possible. It is believed that the integration of the original phonomyographic signal into the display is a key for the success of this device as a standard in clinical practice. In this manner, a better distinction between artefacts caused by interferences from other devices such as electrocautery or movement artefacts is achieved.

Figure 3:
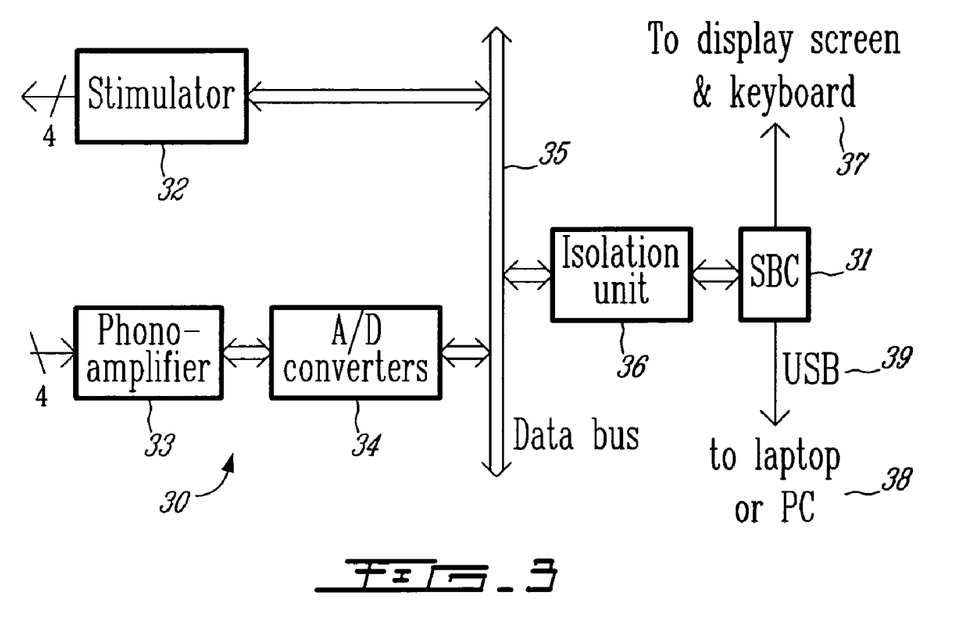
FIG. 3 is a schematic block diagram of another illustrative embodiment of a phonomyographic device for neuromuscular monitoring according to the present invention.

Referring to FIG. 3, a block diagram of a third illustrative embodiment 30 of the phonomyographic device according to the present invention is illustrated. This third embodiment is designed around a commercially available Single-Board Computer (SBC) 31. The SBC 31 provides the following functions:

1. Controls the stimulator 32 and data-acquisition modules (phono-amplifier 33 and A/D converter board 34) via a data bus 35 electrically isolated from the SBC through an isolation unit 36;
2. Performs preliminary analysis of the acquired data (phonomyograms) and displays results;
3. Controls a display screen, for example a liquid crystal display (LCD) and keyboard 37 to provide a graphical user interface; and
4. Connects the system to a personal computer (PC) or laptop computer 38 via an USB port 39.

All the modules shown in FIG. 3, except for the SBC 31, are custom designed. A short description of each module follows.

The isolation unit 36 ensures patient safety in case of equipment malfunction by placing an electrically isolated barrier between the SBC 31 and the system components 32–34 that are in contact with the patient. The isolation unit 36 is implemented with opto-couplers and serializer/deserializer circuits to provide a subset of the address, data and control buses of the SBC 31 to the left side of the isolation barrier (also referred to as the patient side of the barrier).

The bus structure 35 gives flexibility to the device, since other modules can be added to upgrade the system. To maintain the effectiveness of the isolation unit 36, all circuits located on the patient side of the barrier must be powered by batteries or by a medical-grade (i.e. low leakage) power supply. Circuits on the right side of the barrier can be powered by conventional power supplies or, if a PC 38 is used, via the USB port 39.

The stimulator 32 has four independent outputs and can generate current pulses of programmable amplitude, width, and repetition rate. Several modes of stimulation (for example, titanic and trains-of-four) can be selected from the user interface. Up to four different muscles can thus be activated in any predefined pattern.

The data-acquisition module comprises a 4-channel phono-amplifier 33 and A/D converter board 34. The inputs of the phono-amplifier 33 are phonomyographic signals from condenser microphones (not shown) located on the muscles being monitored. Each channel of the phono-amplifier 33 consists of an instrumentation amplifier and an active band-pass filter. The gains of the channel amplifiers and cut-off frequencies of the filters are individually programmable. The A/D converter board 34 uses a "chip" capable of simultaneously sampling 4 signals and performing, for example, up to 6 million conversions per second with 12 bits resolution. The chip also contains a 16-samples deep First-In-First-Out (FIFO) memory and a flexible device controller that allows many scanning modes. The built-in FIFO memory significantly reduces timing constraints between the AND converter board 34 and the isolated data bus 35 and reduces the risk of data loss.

The software that is used in the illustrative embodiments of the phonomyographic device can be the software LabVIEW™. This graphical programming langage allows to create an user-friendly and easy-to-use user interface.

Figure 4A:
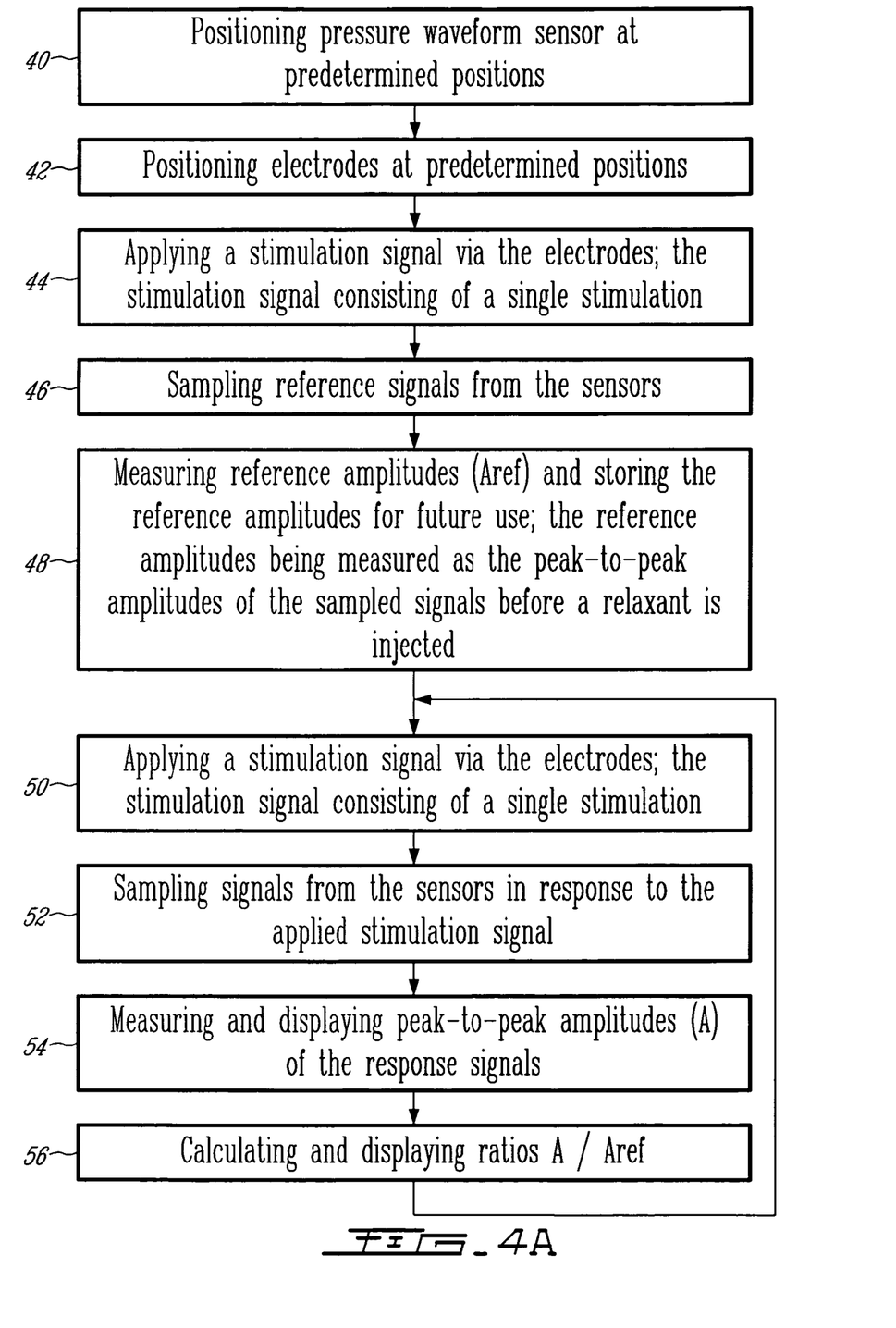
FIG. 4A is a flow chart of a first illustrative embodiment of phonomyographic method for neuromuscular monitoring that can be implemented by the illustrative embodiments of phonomyographic device in accordance with the present invention.
Figure 4B:
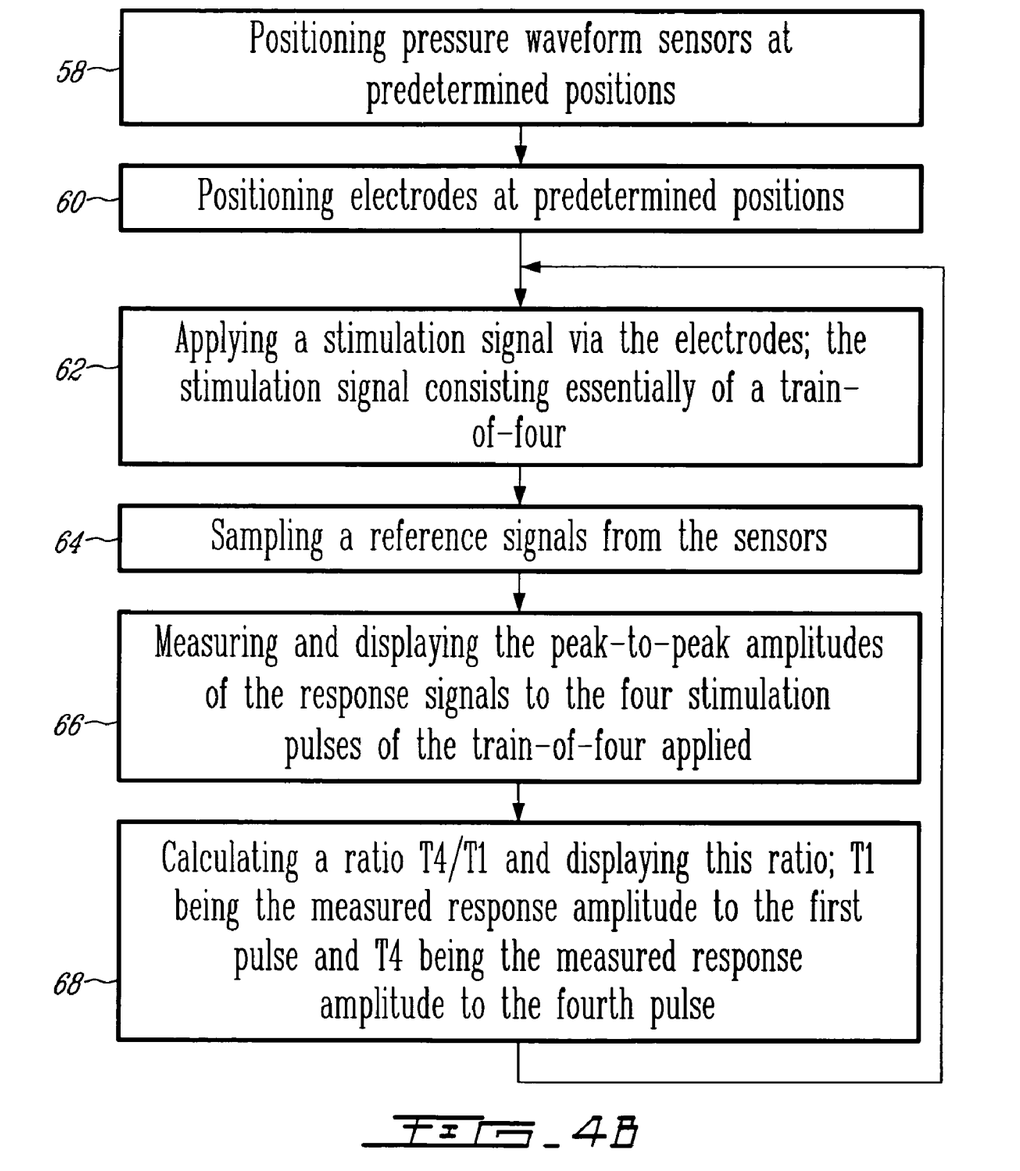
FIG. 4B is a flow chart of a second illustrative embodiment of a phonomyographic method for neuromuscular monitoring that can be implemented by the illustrative embodiments of phonomyographic device in accordance with the present invention.

FIGS. 4A and 4B are flow charts of illustrative embodiments of phonomyographic methods for neuromuscular monitoring that can be implemented by the above described illustrative embodiments of the phonomyographic device according to the present invention.

Referring to FIG. 4A, a phonomyographic method for neuromuscular monitoring using a single stimulation strategy will be described.

The first step 40 is the positioning of the pressure waveform sensors at predetermined positions on the patient's body. Then, in step 42, the stimulation electrodes are also placed on the patient's body.

First, a reference signal is acquired before the injection of a relaxant. To do this, a single stimulation signal is applied via the stimulation electrodes (step 44) and the reference signals from the pressure waveform sensors are then sampled (step 46) and their peak-to-peak amplitudes ($A_{ref}$) are measured and stored (step 48).

After the relaxant is injected, its effects are measured by repeatedly applying single stimulation signals, measuring the response signals and comparing these response signals to the reference signals.

More specifically, the single stimulation signal is applied via the electrodes (step 50) and the signals produced in response to the applied single stimulation signal are sampled in step 52.

In step 54, the peak-to-peak amplitudes (A) of the response signals are measured and displayed. Finally, the ratios $A/A_{ref}$ are calculated and displayed (step 56). The method then loops back to step 50.

Referring to FIG. 4B, a phonomyographic method for neuromuscular monitoring using a "train of four" stimulation strategy will be described.

Again the first step 58 consists of positioning the pressure waveform sensors at predetermined positions on the patient's body. Then, in step 60, the electrodes are also placed on the patient's body.

The train-of-four stimulation signals are applied via the electrodes (step 62) and the signals produced in response to the applied stimulation train-of-four are sampled in step 64.

In step 66, the peak-to-peak amplitudes of the response signals are measured and displayed. A ratio (T4/T1) of the amplitude of the response signal to the fourth pulse of the train-of-four (T4) over the amplitude of the response signal to the first amplitude of the train-of-four (T1) is then calculated and displayed (step 68).

The method then loops back to step 62.

In other words, the phonomyographic signals are sampled from the sensors and displayed through a real-time graphical display. The low frequency bandwidth within which the phonomyographic muscle responses are detected through the microphone extend between 2 and 10 Hz. The signals from the two microphones are also analysed to obtain real-time data related to muscular relaxation. This constitutes a real-time application and the user can adjust at least some parameters.

Visual Display:

Two windows are dedicated to the display of the phonomyographic signals themselves. It is possible to filter the signals (low pass filtering under 60 Hz, power spectrum analysis shows that such a filtering is possible).

Parameters: Some Parameters are Adjustable,

Sampling frequency, best results for 100 or 200 Hz;

Filtering, low-pass frequency is adjustable by user;

Gain (for pre-amplification), noise problems are generated by too high a gain. Best results are obtained with a gain equal to 5;

The measurement window is chosen by the user and the whole signal is analysed, with synchronization between stimulation and signal analysed; this should provide much better results.

Of course, care should be taken about noise sources to obtain a high quality signal and avoid artefacts.

Figure 5:
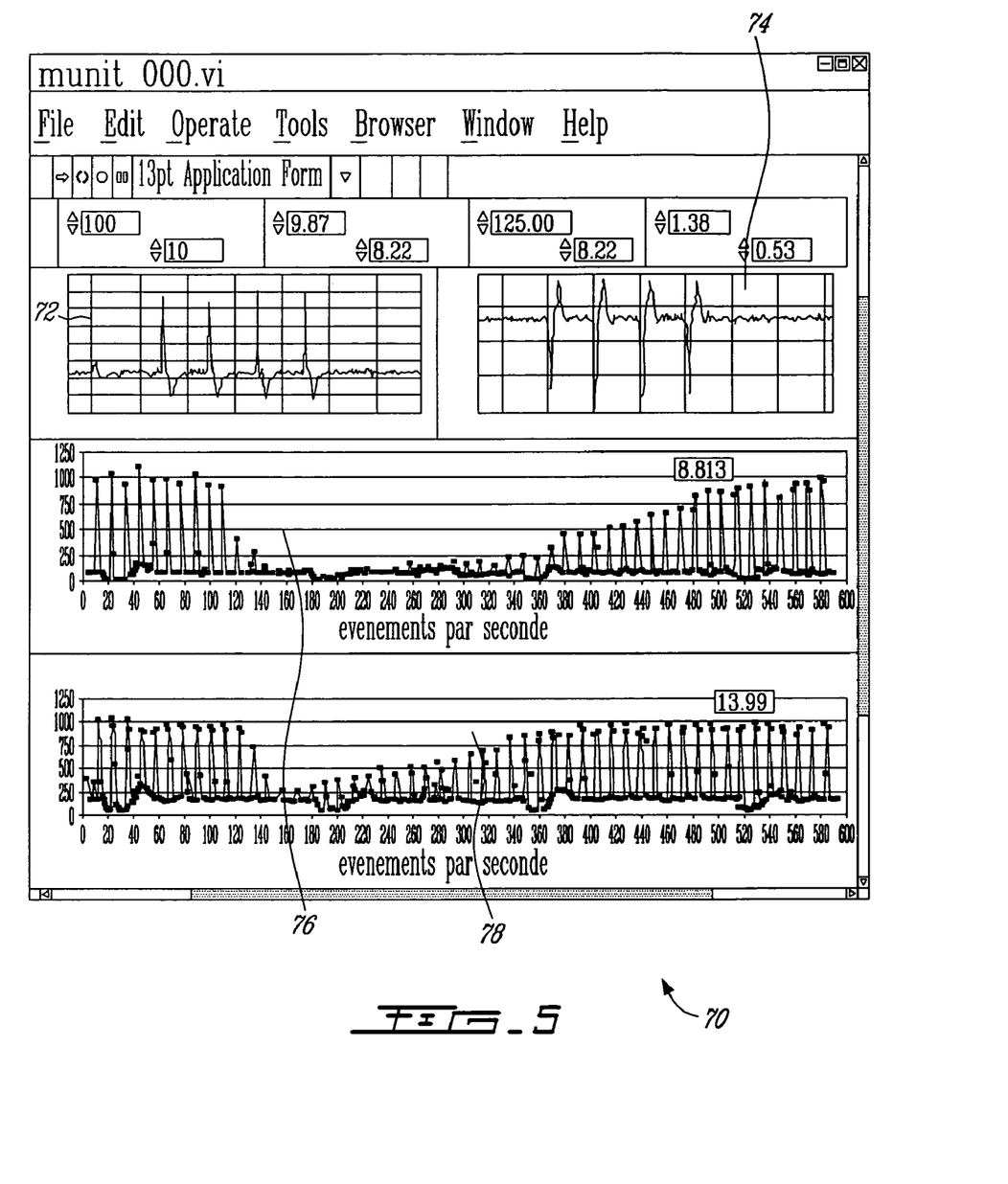
FIG. 5 is an illustrative embodiment of screen shot display.

FIG. 5 is an illustrative embodiment of display 70 that can be used by the phonomyographic devices and methods according to the present invention. In the illustrative embodiment of FIG. 5, the top left window 72 displays, in real time, the sampled phonomyographic signal detected from the adductor pollicis muscle (low frequency signal detected at a frequency of about 8 Hz), and the top right window 74 displays, in real time, the sampled phonomyographic signal from the corrugator supercilii muscle (low frequency signal detected at a frequency of about 3 Hz).

The central 76 and bottom 78 windows display, in real time, graphical trends of muscle relaxation for these two different muscles during, for example, surgery. These data are shown as percentages of muscle relaxation in comparison to "unrelaxed" status before surgery: 100%=no relaxation; 0%=maximal relaxation. More specifically, in the case of a single stimulation, a peak-to-peak amplitude A of the phonomyographic response is displayed in real time; as already indicated, a reference amplitude $A_{ref}$ when the patient is not under relaxant is required to calculate and ultimately display the ratio $A/A_{ref}$. In the case of a train-of-four stimulation, the ratio (T4/T1) between the peak-to-peak amplitude T4 of the phonomyographic response to the last stimulation of the train-of-four versus the peak-to-peak amplitude T1 of the phonomyographic response to the first stimulation is displayed in real time.

Therefore, the illustrative embodiments of the phonomyographic device according to the present invention enable the development of a standard model to use for the evaluation of new muscle relaxants. It also forms a reliable, easy-to-use, but sophisticated neuromuscular monitoring device to be used by every anesthesiologist in daily practice. The additional use of the device as a new tool of intraoperative nerve monitoring in thyroid surgery is also contemplated.

Phonomyography can also be used as a tool in intraoperative monitoring of the recurrent laryngeal nerve during surgery of the thyroid gland. Nerve damage during surgery of the thyroid gland is a major problem with an occurrence of up to 20% if no intraoperative monitoring is used. Until now, electromyography has mainly been used for intraoperative monitoring of the recurrent laryngeal nerve. A currently used system [[17]–[19]] consists of a surface electrode attached to an endotracheal tube and a commercial nerve stimulator connected to an auditory signal device. The stimulation probe is used to identify the nerve by continuously stimulating at 3 Hz and a signal occurring from the evoked electromyographic potentials at the surface tube electrode. However, this system does not give any visual signal and temporary paralysis does occur.

Phonomyography could be used as an alternative approach. Phonomyography has proved to be highly sensible and easy of use at the larynx. Independent from the endotracheal tube, a monitoring system consisting of a microphone inserted into the vestibular folds just aside the vocal cords and a modified monitoring software, providing not only auditory but also visual signals, has been implemented. Spontaneous signals are continuously recorded and can be used to perform intraoperative monitoring in a new and much more detailed way.

As indicated earlier in the present specification, the phonomyographic device can be designed to use a commercial handheld pocket PC as docking station and display screen, therefore reducing the end costs.

Although non-restrictive, illustrative embodiments of the invention has been described in detail herein and illustrated in the accompanying figures, it is to be understood that the invention is not limited to these precise embodiments and that various changes and modifications may be effected therein without departing from the scope or spirit of the present invention.

REFERENCES

[1] Donati F. "Neuromuscular blocking drugs for the new millennium: current practice, future trends—comparative pharmacology of neuromuscular blocking drugs". Anesth Analg. 2000 May; 90(5 Suppl):S2–6.

[2] Ibebunjo C, Srikant C B, Donati F. "Morphological correlates of the differential responses of muscles to vecuronium". Br J Anaesth. 1999 August;83(2):284–91.

[3] Engbaek J. "Monitoring of neuromuscular transmission by electromyography during anaesthesia. A comparison with mechanomyography in cat and man". Dan Med Bull. 1996 September;43(4):301–16.

[4] Hemmerling T M, Donati F, Beaulieu P, Babin D. "Phonomyography of the corrugator supercilii muscle: signal characteristics, best recording site and comparison with acceleromyography". Br J Anaesth 2002 March; 88 (3): 389–93.

[5] Plaud B, Debaene B, Donati F. "The corrugator supercilii, not the orbicularis oculi, reflects rocuronium neuromuscular blockade at the laryngeal adductor muscles". Anesthesiology. 2001 July;95(1):96–101.

[6] Rimaniol J M, Dhonneur G, Sperry L, Duvaldestin P. "A comparison of the neuromuscular blocking effects of atracurium, mivacurium, and vecuronium on the adductor pollicis and the orbicularis oculi muscle in humans". Anesth Analg. 1996 October;83(4):808–13.

[7] McCluskey A, Meakin G, Hopkinson J M, Baker R D. "A comparison of acceleromyography and mechanomyography for determination of the dose-response curve of rocuronium in children". Anaesthesia. 1997 April;52(4): 345–9.

[8] Mortensen C R, Berg H, el-Mahdy A, Viby-Mogensen J. "Perioperative monitoring of neuromuscular transmission using acceleromyography prevents residual neuromuscular block following pancuronium". Acta Anaesthesiol Scand. 1995 August;39(6):797–801.

[9] Frangioni J V, Kwan-Gett T S, Dobrunz L E, McMahon T A. "The mechanism of low-frequency sound production in muscle". Biophys J. 1987 May;51(5):775–83.

[10] Dascalu A, Geller E, Moalem Y, Manoah M, Enav S, Rudick Z. "Acoustic monitoring of intraoperative neuromuscular block". Br J Anaesth. 1999 September;83(3): 405–9.

[11] Bellemare F, Couture J, Donati F, Plaud B. "Temporal relation between acoustic and force responses at the adductor pollicis during nondepolarizing neuromuscular block". Anesthesiology. 2000 September;93(3):646–52.

[12] Hemmerling T M, Donati F, Beaulieu P, Babin D. "Phonomyography of the corrugator supercilii muscle: signal characteristics, best recording site and comparison with acceleromyography". Br J Anaesth 2002 March; 88 (3): 389–93

[13] Hemmerling T M, Donati F, Beaulieu P, Babin D. "Duration of control stimulation does not affect onset and offset of neuromuscular blockade at the corrugator sueprcilii muscle measured with phonomyography or acceleromyography". Can J Anaesth 2002. in press

[14] Hemmerling T M, Babin D, Donati F. Phonomyography is a novel method to determine neuromuscular blockade at the laryngeal adductor muscles: comparison with the cuff-pressure method". Anesthesiology.in press

[15] Hemmerling T M, Babin D, Donati F. "Phonomyography and Mechanomyography can be used interchangeably to measure neuromuscular blockade at the corrugator supercilii muscle". ASA abstract 2002.

[16] Hemmerling T M, Babin D, Donati F. "Phonomyography and Mechanomyography can be used interchangeably to measure neuromuscular blockade at the adductor pollicis muscle". ASA abstract 2002.

[17] Hemmerling T M, Schmidt J, Bosert C, Jacobi K E, Klein P. "Intraoperative monitoring of the recurrent laryngeal nerve in 151 consecutive patients undergoing thyroid surgery". Anesth Analg. 2001 August;93(2):396–9.

[18] Kastl S, Hemmerling T M, Schmidt J, Kat S, Hohenberger W, Klein P. "Electromyographic nerve identification during resection of an intrathoracic goiter via a right anterolateral thoracotomy using a novel method". Surgery. 2001 July;130(1):93–6. No abstract available.

[19] Hemmerling T M, Schurr C, Dern S, Schmidt J, Braun G G, Klein P. "Intraoperative electromyographic recurrent laryngeal nerve identification as a routine measure". Chirurg. 2000 May;71(5):545–50 (German).

What is claimed is:

1. A system using phonomyography for monitoring relaxation of a given muscle of a living subject, comprising:
means for applying muscle-activating stimulation signals to the living subject's body via at least one electrode to stimulate the given muscle of the living subject;
means for sensing pressure waveform signals produced by the given muscle of the living subject in response to the applied stimulation signals;
means for processing the sensed pressure waveform signals to produce data indicative of a level of relaxation of the given muscle of the living subject; and
means for displaying the data indicative of the level of relaxation of the given muscle of the living subject from the processing means.

2. A system using phonomyography for monitoring relaxation of a given muscle of a living subject, comprising:
at least one neurostimulator to apply muscle-activating stimulation signals to the living subject's body via at least one electrode to stimulate the given muscle of the living subject;
at least one pressure waveform sensor to detect pressure waveform signals produced by the given muscle of the living subject in response to the applied stimulation signals;
a processor of the detected pressure waveform signals to produce data indicative of a level of relaxation of the given muscle of the living subject; and
a display of the data indicative of the level of relaxation of the given muscle of the living subject from the processor.

3. The system of claim 2, wherein the data displayed through the display is selected from the group consisting of: raw pressure waveform signals detected through said at least one pressure waveform sensor, amplitudes of the pressure waveform signals, and ratios of said amplitudes.

4. The system of claim 2, further comprising an amplifier for amplifying the pressure waveform signals detected by said at least one pressure waveform sensor.

5. The system of claim 2, comprising a controller connected to said at least one neurostimulator and to said at least one pressure waveform sensor, said controller incorporating the processor and display.

6. The system of claim 5, wherein the controller includes a laptop computer.

7. The system of claim 5, wherein said controller includes a pocket computer.

8. The system of claim 2, wherein said at least one neurostimulator includes a plurality of neurostimulators respectively associated to different muscles of the living subject.

9. The system of claim 2, wherein said at least one pressure waveform sensor includes a plurality of pressure waveform sensors respectively associated to different muscles of the living subject.

10. The system of claim 2, wherein said at least one pressure waveform sensor has a detection frequency bandwidth ranging from about 2 Hz to about 10 Hz.

11. The system of claim 10, wherein said at least one pressure waveform sensor comprises at least one microphone.

12. The system of claim 2, wherein the muscle-activating stimulation signals comprises single stimulation signals.

13. A neuromuscular monitoring system using phonomyography, comprising:
   at least one neurostimulator to apply muscle-activating stimulation signals to a patients body via at least one electrode;
   at least one pressure waveform sensor to detect pressure waveform signals produced by a patient's muscle in response to the applied stimulation signals; and
   a controller connected to said at least one neurostimulator and to said at least one pressure waveform sensor, said controller including a processor of the detected pressure waveform signals and a display of data, from the processor, related to the detected pressure waveform signals;
   wherein the controller is so configured as to:
      before the administration of a relaxant to the patient:
         apply a predetermined muscle-activating stimulation signal to the patient's body through said at least one neurostimulator and via said at least one electrode;
         sample the pressure waveform signal detected by said at least one pressure waveform sensor in response to the applied predetermined stimulation signal; and
         measure a reference amplitude ($A_{ref}$) of the sampled signal; and
      after a relaxant has been administered to the patient:
         apply the predetermined muscle-activating stimulation signal through said at least one neurostimulator and via said at least one electrode;
         sample the pressure waveform signal detected by said at least one pressure waveform sensor in response to the applied predetermined stimulation signal;
         measure an amplitude (A) of the response signal;
         calculate a ratio $A/A_{ref}$; and
         display the calculated ratio.

14. A neuromuscular monitoring system using phonomyography, comprising:
   at least one neurostimulator to apply muscle-activating stimulation signals to a patient's body via at least one electrode;
   at least one pressure waveform sensor to detect pressure waveform signals produced by a patient's muscle in response to the applied stimulation signals: and
   a processor of the detected pressure waveform signals and a display of data, from the processor, related to the detected pressure waveform signals;
wherein the muscle-activating stimulation signals comprise train-of-four twitches.

15. A neuromuscular monitoring system using phonomyography, comprising:
   at least one neurostimulator to apply muscle-activating stimulation signals to a patient's body via at least one electrode;
   at least one pressure waveform sensor to detect pressure waveform signals produced by a patient's muscle in response to the applied stimulation signals; and
   a controller connected to said at least one neurostimulator and to said at least one pressure waveform sensor, said controller including a processor of the detected pressure waveform signals and a display of data, from the processor, related to the detected pressure waveform signals;
   wherein the muscle-activating stimulation signals comprise train-of-four twitches, and wherein the controller is so configured as to:
      measure a peak-to-peak amplitude of a pressure waveform signal detected by said at least one pressure waveform sensor in response to a first pulse of the train-of-four (T1);
      measure a peak-to-peak amplitude of a pressure waveform signal detected by said at least one pressure waveform sensor in response a fourth pulse of the train-of-four (T4);
      calculate a ratio T4/T1; and
      display the calculated ratio.

16. A neuromuscular monitoring method using phonomyography, comprising:
   providing at least one pressure waveform sensor;
   positioning said at least one pressure waveform sensor at a predetermined position of a patient's body;
   providing at least one electrode;
   positioning said at least one electrode at a predetermined position of the patient's body;
   applying a muscle-activating stimulation signal to the patient's body via said at least one electrode;
   sampling a pressure waveform signal detected by said at least one pressure waveform sensor in response to the applied muscle-activating stimulation signal;
   measuring a reference amplitude ($A_{ref}$) of the sampled signal;
   after a relaxant has been administered:
      applying a subsequent muscle-activating stimulation signal to the patient's body via said at least one electrode;
      sampling a subsequent pressure waveform signal detected by said at least one pressure waveform sensor in response to the subsequent muscle-activating stimulation signal;
      measuring an amplitude (A) of the subsequent pressure waveform signal;
      calculating a ratio $A/A_{ref}$; and
      displaying the calculated ratio.

17. The neuromuscular monitoring method of claim 16, wherein applying a muscle-activating stimulation signal comprises applying a single pulse stimulation signal.

18. The neuromuscular monitoring method of claim 16, wherein measuring an amplitude comprises measuring a peak-to-peak amplitude.

19. A method using phonomyography for monitoring relaxation of a muscle of a living subject, comprising:
   providing at least one pressure waveform sensor;
   positioning said at least one pressure waveform sensor at a first predetermined position of the living subject's body;
   providing at least one electrode;

positioning the at least one electrode at a predetermined second position of the living subject's body;

applying muscle-activating stimulation signals to the living subject's body via said at least one electrode to stimulate the given muscle of the living subject;

sampling pressure waveform signals detected by said at least one pressure waveform sensor and produced by the given muscle of the living subject in response to the applied muscle-activating stimulation signals;

processing the sampled detected pressure waveform signals to produce data indicative of a level of relaxation of the given muscle of the living subject; and displaying the data indicative of the level of relaxation of the given muscle of the living subject from the act of processing.

20. The method of claim 19, wherein:

processing the sampled detected pressure waveform signals comprises measuring amplitudes of the detected pressure waveform signals; and displaying data comprises displaying the detected pressure waveform signals and the measured amplitudes.

21. A neuromuscular monitoring method using phonomyography, comprising:

providing at least one pressure waveform sensor;

positioning said at least one pressure waveform sensor at a predetermined position of a patient's body;

providing at least one electrode;

positioning the at least one electrode at a predetermined position of the patient's body;

applying muscle-activating stimulation signals to the patient's body via said at least one electrode;

sampling pressure waveform signals detected by said at least one pressure waveform sensor in response to the applied muscle-activating stimulation signals;

processing the detected pressure waveform signals; and displaying data, from the act of processing, related to the detected pressure waveform signals;

wherein applying muscle-activating stimulation signals comprises applying train-of-four twitches.

22. A neuromuscular monitoring method using phonomyography, comprising:

providing at least one pressure waveform sensor;

positioning said at least one pressure waveform sensor at a predetermined position of a patient's body;

providing, at least one electrode;

positioning the at least one electrode at a predetermined position of the patient's body;

applying muscle-activating stimulation signals to the patient's body via said at least one electrode;

sampling pressure waveform signals detected by said at least one pressure waveform sensor in response to the applied muscle-activating stimulation signals;

processing the sampled detected pressure waveform signals; and displaying data, from the act of processing, related to the detected pressure waveform signals;

wherein:

processing the sampled detected pressure waveform signals comprises measuring amplitudes of the detected pressure waveform signals; and displaying data comprises displaying the detected pressure waveform signals and the measured amplitudes; and wherein applying muscle-activating stimulation signals comprises applying train-of-four twitches, and wherein measuring amplitudes of the detected pressure waveform signals comprises:

measuring a peak-to-peak amplitude of the pressure waveform signal detected by said at least one pressure waveform sensor in response to a first pulse of each train-of-four (T1);

measuring a peak-to-peak amplitude of the pressure waveform signal detected by said at least one pressure waveform sensor in response to a fourth pulse of the same train-of-four (T4); and calculating a ratio T4/T1.

23. The neuromuscular monitoring method of claim 22, wherein displaying the measured amplitudes comprises displaying the T4/T1 calculated ratio.

* * * * *